United States Patent [19]

Shuber

[11] Patent Number: 5,589,330
[45] Date of Patent: Dec. 31, 1996

[54] HIGH-THROUGHPUT SCREENING METHOD FOR SEQUENCE OR GENETIC ALTERATIONS IN NUCLEIC ACIDS USING ELUTION AND SEQUENCING OF COMPLEMENTARY OLIGONUCLEOTIDES

[75] Inventor: Anthony P. Shuber, Millford, Mass.

[73] Assignee: Genzyme Corporation, Cambridge, Mass.

[21] Appl. No.: 281,940

[22] Filed: Jul. 28, 1994

[51] Int. Cl.[6] .............................. C12Q 1/68; C12Q 1/70; C12P 19/34
[52] U.S. Cl. ................... 435/5; 435/6; 435/91.1; 435/91.2
[58] Field of Search .................. 435/5, 6, 91.1, 435/91.2; 935/78

[56] References Cited

U.S. PATENT DOCUMENTS

| | | | |
|---|---|---|---|
| 5,403,709 | 4/1995 | Agrawal et al. | 435/6 |
| 5,434,049 | 7/1995 | Okano et al. | 435/6 |

OTHER PUBLICATIONS

Shuber et al., *Am. J. Human Genet.* 57 (4 Suppl.), 228 (Abstract).
Chehab et al., *Hum. Genet.* 89, 163–168 (1992).
Verlaan–de Vries et al., *Gene* 50, 313–320 (1986).
Porumb et al., *Meth. Mol. Cell. Biol.* 4, 10–21 (1993).
Chehab et al., (1987), *Nature*, 329:293–294.
Haliassos et al., (1989), *Nucleic Acids Research*, 17:3606.
Maxam, A. M., (1977), *Prac. Natl. Acad. Sci., USA*, 74 [2]:560–564.
Mayall et al., (1990), *J. Med. Genet.*, 27:658.
Richards, B., et al., (1993), *Human Mol. Genetics*, 2 [2]:159–163.
Rommens et al., (1980), *Am J. Hum. Genet.*, 46:395–396.
Saiki, R. K. et al., (1986), *Nature*, 324:163–166.
Saiki, R. K. et al., (1988), *Science*, 239:487–491.
Sanger et al., (1977), *Proc. Natl. Acad. Sci. USA*, 74:5463.
Southern, E. M., (1975), *J. Mol. Biol.*, 98:503–517.
Wood et al., (1985), *Proc. Natl. Acad. Sci., USA* 82:1585.
Wyman et al., (1980), *Proc. Natl. Acad. Sci. USA*, 7:6754–6758.
Shuber et al., (1993), *Human Molecular Genetics*, 2 [2]:153–158.

*Primary Examiner*—Kenneth R. Horlick
*Attorney, Agent, or Firm*—Darby & Darby, P. C.

[57] ABSTRACT

The present invention pertains to high-throughput screening methods to identify genetic alterations in DNA samples. A multiplicity of DNA samples are immobilized on a solid support and hybridized simultaneously with a mixture of oligonucleotides representing variant sequences. Hybridizing oligonucleotides are then eluted from each DNA sample individually and their sequence is determined. The methods of the present invention allow the identification of disease-causing mutations and polymorphisms in patients' DNA, as well as the identification of disease-causing microorganisms.

18 Claims, 4 Drawing Sheets

Phase I Results

Dot Blot Results Generated from Combinatorial Hybridization

A panel of different patient samples hybridized with pools of mutation specific oligonucelotides

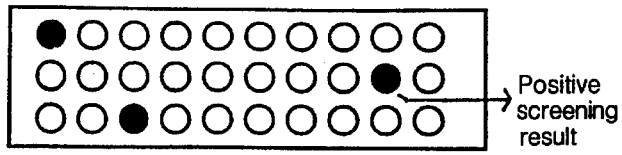

→ Positive screening result

↓ Identification of specific mutations

Positives Punched Out and Placed into Epp. Tubes (30 min.)

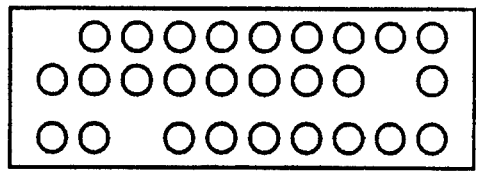 → 

↓

Oligos Eluted Off of Solid Support (15 min.)

↓

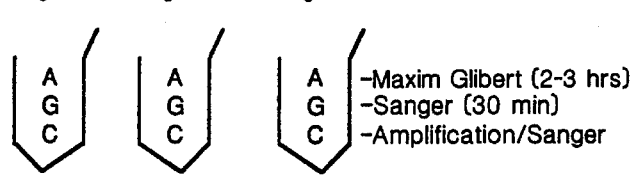

—Maxim Glibert (2-3 hrs)
—Sanger (30 min)
—Amplification/Sanger

Chemical or Enzymatic Sequencing Reactions

↓

Reactions Loaded onto Automated Sequencer

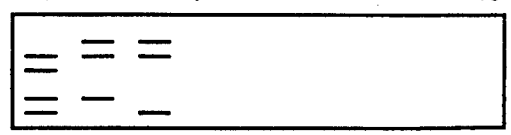

Sample Capacity= ~240 samples/hr

↓

Software Analysis    Mutation Results (Next Day)

FIG.4

HIGH-THROUGHPUT SCREENING METHOD FOR SEQUENCE OR GENETIC ALTERATIONS IN NUCLEIC ACIDS USING ELUTION AND SEQUENCING OF COMPLEMENTARY OLIGONUCLEOTIDES

FIELD OF THE INVENTION

This invention pertains to the identification of specific disease-causing DNA sequences in mammals. The methods of the present invention can be used to identify genetic polymorphisms, to determine the molecular basis for genetic diseases, and to provide carrier and prenatal diagnosis for genetic counseling. Furthermore, the invention pertains to specific high-resolution identification of disease-causing microorganisms in mammals.

BACKGROUND OF THE INVENTION

The ability to detect differences in DNA sequence (i.e. mutations) is central to the diagnosis of genetic diseases and to the identification of clinically significant variants of disease-causing microorganisms. One method for the molecular analysis of genetic variation involves the detection of restriction fragment length polymorphisms (RFLPs) using the Southern blotting technique (Southern, E. M., J. Mol. Biol., 98:503–517, 1975; Kan et al., Nature, 313:369–374, 1978; Wyman et al. Proc. Natl. Acad. Sci. USA, 77:6754–6758, 1980). Since this approach is relatively cumbersome, new methods have been developed, some of which are based on the polymerase chain reaction (PCR). These include: RFLP analysis using PCR (Chehab et al., Nature, 329:293–294, 1987; Rommens et al., Am. J. Hum. Genet., 46:395–396, 1990), the creation of artificial RFLPs using primer-specified restriction-site modification (Haliassos et al., Nucleic Acids Research, 17:3606, 1989), and hybridization to allele-specific oligonucleotides (ASOs) (Saiki et al., Nature, 324:163–166 (1986).

These methods are limited in their applicability to complex mutational analysis. For example, in cystic fibrosis, a recessive disorder affecting 1 in 2000–2500 live births in the United States, more than 225 presumed disease-causing mutations have been identified. Furthermore, multiple mutations may be present in a single affected individual, and may be spaced within a few base pairs of each other. These phenomena present unique difficulties in designing clinical screening methods that can accommodate large numbers of sample DNAs.

In U.S. patent application Ser. No. 07/957,205, abandoned and in Shuber et al., Human Molecular Genetics, 2:153–158, 1993, the present inventors disclose a method that allows the simultaneous hybridization of multiple oligonucleotide probes to a single target DNA sample. By including in the hybridization reaction an agent that eliminates the disparities in melting temperatures of hybrids formed between synthetic oligonucleotides and target DNA, it is possible in a single test to screen a DNA sample for the presence of different mutations. Typically, more than 50 ASOs can be pooled and hybridized to target DNA; in a second step, ASOs from a pool giving a positive result are individually hybridized to the same DNA.

This methodology is, however, limited by the necessity of performing subsequent multiple individual hybridizations to identify the relevant ASO from the pool. Thus, there is a need in the art for relatively low cost methods that allow the efficient screening of large numbers of DNA samples for genetic variation and the rapid identification of the variant sequence.

SUMMARY OF THE INVENTION

The present invention encompasses high-throughput methods for detecting genetic alterations (defined as nucleotide additions, deletions, or substitutions) in a large number of DNA samples, which is achieved by: immobilizing the DNA samples to a solid-phase support; simultaneously hybridizing to the DNA a multiplicity of synthetic oligonucleotides of equivalent length, wherein each oligonucleotide comprises a variant of a known sequences in the DNA samples; removing oligonucleotides that do not hybridize; eluting hybridized oligonucleotides and separating them from the immobilized DNA; and, finally, determining the sequence of the eluted oligonucleotides.

In accordance with the present invention, both the target DNA and/or the eluted oligonucleotides may be amplified using the polymerase chain reaction (PCR) to facilitate detection and sequencing. Importantly, hybridizations are carded out under conditions that minimize the differences in melting temperature of DNA:DNA hybrids formed between different oligonucleotides and the target DNA.

BRIEF DESCRIPTION OF THE DRAWINGS

FIG. 4 shows a schematic representation of the methods of the present invention.

DETAILED DESCRIPTION OF THE INVENTION

Figure 1:
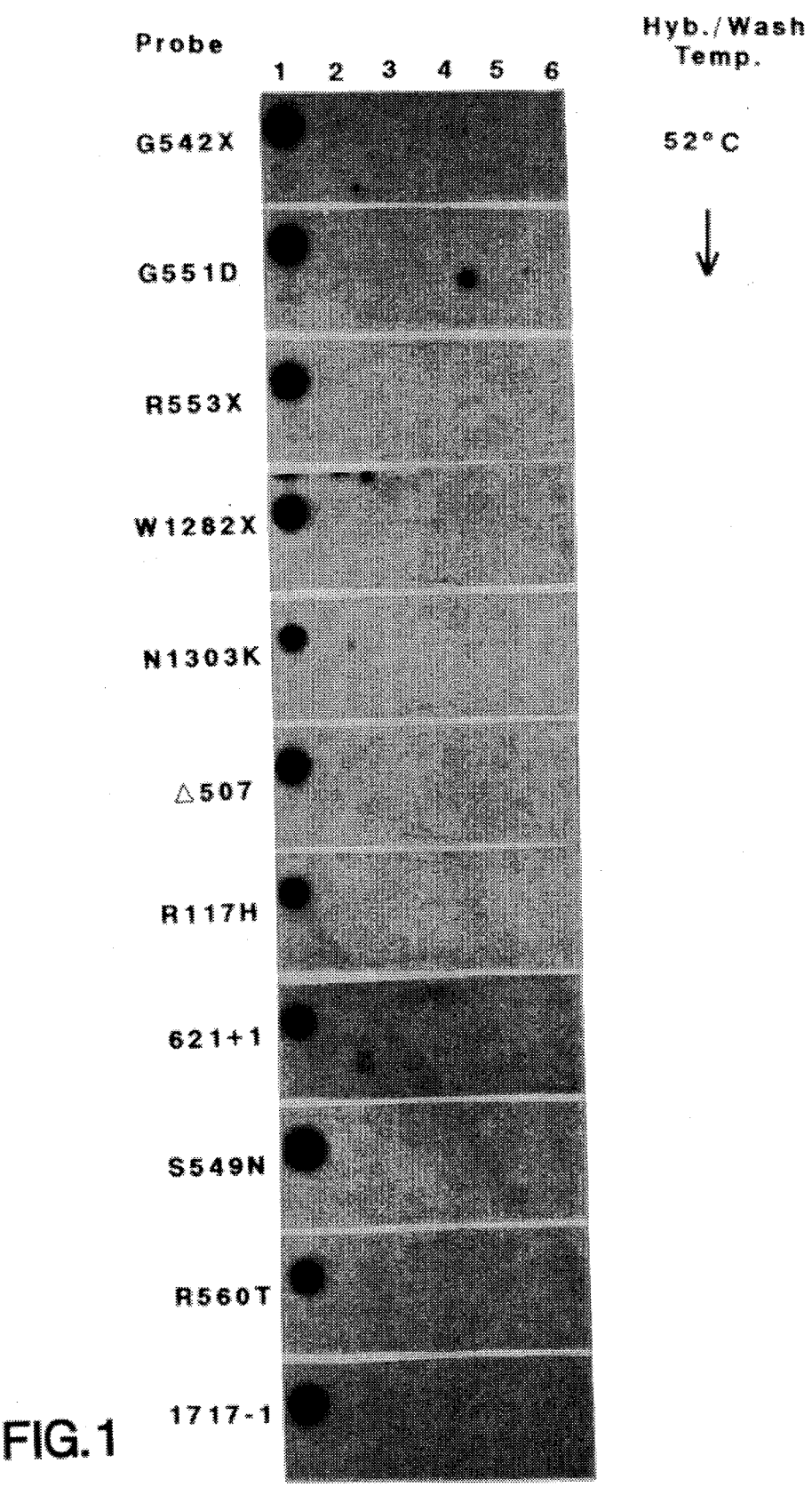
FIG. 1 shows autoradiographic results obtained from hybridizing multiple identical filters containing human genomic DNA with $^{32}$P-labelled ASOs specific for different alleles of the cystic fibrosis transmembrane regulator (CFTR) gene. The ASOs used in each hybridization are identified on the left of each filter. Lane 1 in each case contains DNA carrying the mutant sequence complementary to each ASO; lanes 2–6 contain wild-type "normal" sequences.
Figure 2A:
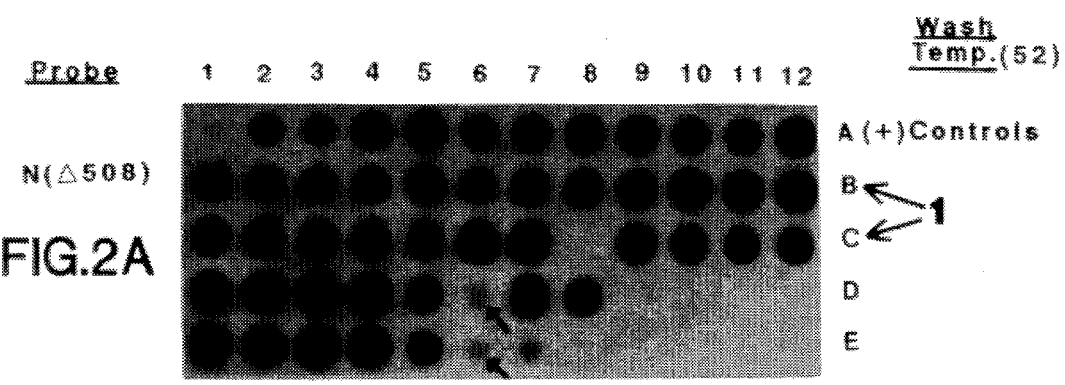
FIG. 2 shows autoradiographic results obtained from hybridizing four identical filters containing human genomic DNA with $^{32}$P-labelled ASOs specific for different alleles of the cystic fibrosis transmembrane regulator (CFTR) gene. The ASOs used in each hybridization are identified on the left of each filter. The lanes marked A contain positive control DNA samples. Rows B–E contain patient samples analyzed in duplicate, with the exception of 8C (amplification failure on duplicate sample), and D7, D8 and E7 (positive controls.)
Figure 2B:
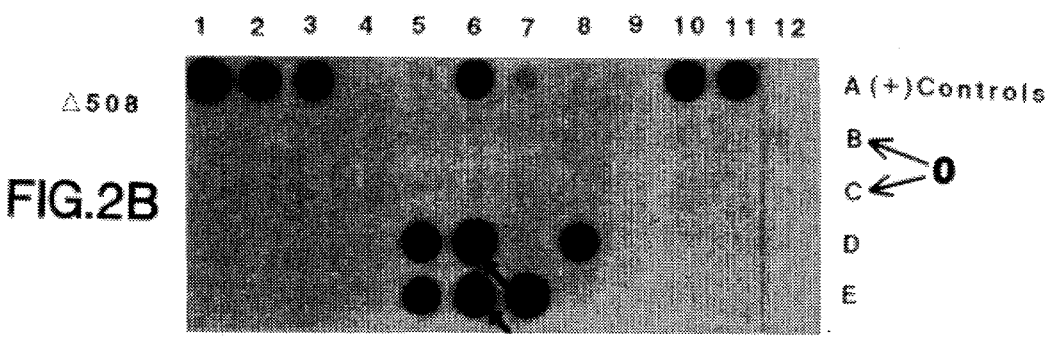
Figure 2C:
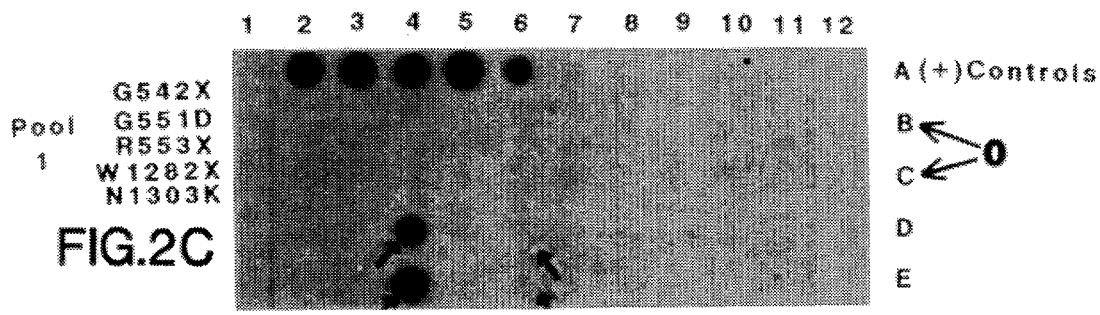
Figure 2D:
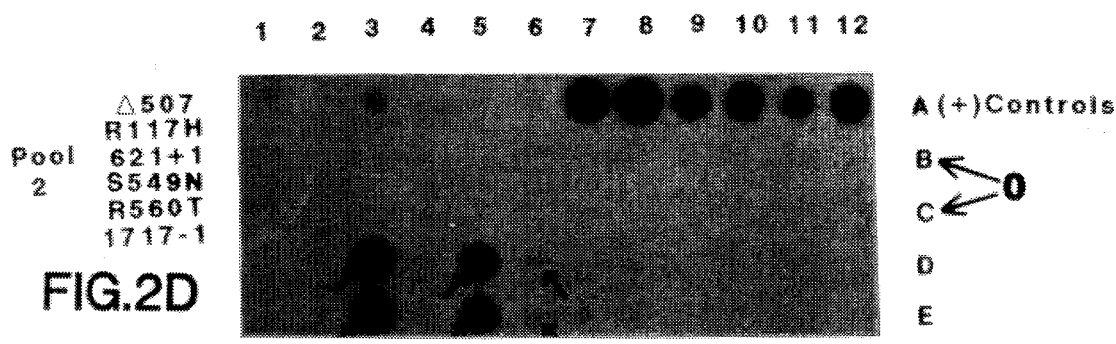

All patent applications, patents, and literature references cited in this specification are hereby incorporated by reference in their entirety. In case of conflict, the present description, including definitions, will control.

Definitions

1. An "allele-specific oligonucleotide" (ASO) as defined herein is an oligonucleotide having a sequence that is identical or almost identical to a known segment of DNA. Often, an ASO contains a small change relative to the prevalent "wild type" sequence. This change may comprise addition, deletion, or substitution of one or more nucleotides. ASOs can be designed to identify any addition, deletion, or substitution, as long as the DNA sequence is known.

2. A "variant" sequence as used herein encompasses a DNA sequence that differs from a known sequence by the addition, deletion, or substitution of one or more nucleotides.

3. "Amplification" of DNA as used herein denotes the use of polymerase chain reaction (PCR) to increase the concentration of a particular DNA sequence within a mixture of DNA sequences. For a description of PCR see Saiki et al., Science 239:487 (1988).

4. "Chemical sequencing" of DNA denotes methods such as that of Maxim and Gilbert (Maxim-Gilbert sequencing, Maxam and Gilbert, 1977, Proc. Natl. Acad. Sci. USA 74:560), in which DNA is randomly cleaved using individual base-specific reactions.

5. "Enzymatic sequencing" of DNA denotes methods such as that of Sanger (Sanger et al., 1977, Proc. Natl. Acad. Sci. USA, 74:5463), in which a single-stranded DNA is copied and randomly terminated using DNA polymerase.

6. In this specification, the terms "bound" and "hybridized" are used interchangeably to denote the formation of DNA:DNA duplexes. The term "affinity purified" denotes purification using hybridization.

7. "High-throughput" denotes the ability to simultaneously process and screen a large number of DNA samples (e.g. in excess of 100 genomic DNAs) in a rapid and economical manner.

The present invention encompasses a high-throughput method for identifying specific DNA sequences in DNA isolated from a patient. The method is applicable when one or more genes or genetic loci are targets of interest.

In one embodiment, the specific DNA sequence comprises a portion of a particular gene or genetic locus in the patient's genomic DNA known to be involved in a pathological condition or syndrome. Non-limiting examples include cystic fibrosis, sickle-cell anemia, β-thalassemia, and Gaucher's disease.

In another embodiment, the specific DNA sequence comprises part of a particular gene or genetic locus that may not be known to be linked to a particular disease, but in which polymorphism is known or suspected.

In yet another embodiment, the specific DNA sequence comprises part of a foreign genetic sequence e.g. the genome of an invading microorganism. Non-limited examples include bacteria and their phages, viruses, fungi, protozoa, and the like. The present methods are particularly applicable when it is desired to distinguish between different variants or strains of a microorganism in order to choose appropriate therapeutic interventions.

In accordance with the present invention, the target DNA represents a sample of DNA isolated from a patient. This DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection or inflammation. DNA is extracted from the cell source or body fluid using any of the numerous methods that are standard in the art. It will be understood that the particular method used to extract DNA will depend on the nature of the source. The minimum amount of DNA to be extracted for use in the present invention is about 25 pg (corresponding to about 5 cell equivalents of a genome size of $4 \times 10^9$ base pairs).

Once extracted, the target DNA may be employed in the present invention without further manipulation. Alternatively, one or more specific DNA regions present in the target DNA may be amplified by PCR. In this case, the amplified regions are specified by the choice of particular flanking sequences for use as primers. Amplification at this step provides the advantage of increasing the concentration of specific DNA sequences within the target DNA sequence population. The length of DNA sequence that can be amplified ranges from 80 bp to up to 30 kbp (Saiki et al., 1988, Science, 239:487).

In one embodiment, the target DNA, with or without prior amplification of particular sequences, is bound to a solid-phase matrix. This allows the simultaneous processing and screening of a large number of patient samples. Non-limiting examples of matrices suitable for use in the present invention include nitrocellulose or nylon filters, glass beads, magnetic beads coated with agents for affinity capture, treated or untreated microliter plates, and the like. It will be understood by a skilled practitioner that the method by which the target DNA is bound to the matrix will depend on the particular matrix used. For example, binding to nitrocellulose can be achieved by simple adsorption of DNA to the filter, followed by baking the filter at 75°–80° C. under vacuum for 15 min–2 h. Alternatively, charged nylon membranes can be used that do not require any further treatment of the bound DNA. Beads and microliter plates that are coated with avidin can be used to bind target DNA that has had biotin attached (via e.g. the use of biotin-conjugated PCR primers.) In addition, antibodies can be used to attach target DNA to any of the above solid supports by coating the surfaces with the antibodies and incorporating an antibody-specific hapten into the target DNA.

In practicing the present invention, the untreated or amplified target DNA, preferably bound to a solid-phase matrix, is incubated with a mixture of allele-specific oligonucleotides (ASOs). 10–200 ASOs can be pooled for a single hybridization, preferably 50–100 and most preferably 50. The length of individual ASOs may be 16–25 nucleotides, preferably 17 nucleotides in length.

The ASOs may be synthesized chemically by methods that are standard in the art, e.g. using commercially available automated synthesizers. ASOs may then be radioactively labelled (e.g. end-labelled with $^{32}P$ using polynucleotide kinase) or conjugated to other commonly used "tags" or reporter molecules. For example, fluorochromes (such as FITC or rhodamine), enzymes (such as alkaline phosphatase), biotin, or other well-known labelling compounds may be attached directly or indirectly. Furthermore, using standard methods, a large number of randomly permuted ASOs can be synthesized in a single reaction. As detailed below, the present invention does not require that individual hybridizing sequences be determined prior to the hybridization. Rather, the sequence of bound ASOs can be determined in a later step.

As described in U.S. patent application Ser. No. 07/957, 205 (filed Oct. 6, 1992, abandoned) and in Shuber et al., 1993, Human Molecular Genetics, 2:153–158, the hybridization reaction is performed under conditions in which ASOs containing different sequences hybridize to their complementary DNA with equivalent strength. This is achieved by: 1) employing ASOs of equivalent length; and 2) including in the hybridization mixture appropriate concentrations of one or more agents that eliminate the disparity in melting temperatures among ASOs of identical length but different guanosine+cytosine (G+C) compositions. Agents that may be used for this purpose include without limitation quaternary ammonium compounds such as tetramethylammonium chloride (TMAC).

TMAC acts through a non-specific salt effect to reducing hydrogen-bonding energies between G-C base pairs. At the same time, it binds specifically to A-T pairs and increases the thermal stability of these bonds. These opposing influences have the effect of reducing the difference in bonding energy between the triple-hydrogen bonded G-C based pair and the double-bonded A-T pair. One consequence, as noted above, is that the melting temperature of DNA:DNA hybrids formed in the presence of TMAC is solely a function of the length of the hybrid. A second consequence is an increase in the slope of the melting curve for each probe. Together these effects allow the stringency of hybridization to be increased to the point that single-base differences can be resolved, and non-specific hybridization minimized (Wood et al., 1985, Proc. Natl. Acad. Sci., USA 82:1585.)

It will be apparent to those skilled in the art that any agent that exhibits these properties can be used in practicing the present invention. Such agents can be easily identified by determining melting curves for different test oligonucleotides in the presence and absence of increasing concentrations of the agent. This can be achieved by attaching a target nucleic acid to a solid matrix such as a nylon filter, individually hybridizing radiolabelled oligonucleotides of identical length but different G+C compositions to the filter, washing the filter at increasing temperatures, and measuring the relative amount of radiolabelled probe bound to the filter at each temperature. An agent that, when present in the hybridization and washing steps described above, results in approximately superimposable and steep melting curves for the different oligonucleotides may be used.

In practicing the present invention, the target DNA and ASOs are incubated for sufficient time and under appropriate conditions to achieve maximal specific hybridization and minimal non-specific i.e. background hybridization. The conditions to be considered include the concentration of each ASO, the temperature of hybridization, the salt concentration, and the presence or absence of unrelated DNA.

The concentration of each ASO may range from 0.025 to 0.2 pmol per ml of hybridization solution. When ASOs of known sequence are used, the optimal concentration for each ASO is determined by test hybridizations in which the signal-to-noise ratio (i.e. specific vs. non-specific binding) of each ASO is measured at increasing concentrations of radiolabelled ASO. To further reduce background hybridization, oligonucleotides containing the non-variant (i.e. wild-type) sequence may be included in the reaction mixture at a concentration equivalent to 1–100 times the concentration of the labelled ASO.

The temperature for hybridization is optimized to be as high as possible for the length of the ASOs being used. This can be determined empirically, using the melting curve determination procedure described above. It will be understood by skilled practitioners that determination of optimal time, temperature, ASO concentration and salt concentration should be done in concert.

Following hybridization, unbound ASOs are removed by washing the matrix-bound DNA in a solution containing TMAC or similar compounds, under conditions that preserve perfectly matched DNA:DNA hybrids. Washing conditions i.e. temperature, nature and concentration of salts, and time of washing, are determined empirically as described above. At this stage, the presence of bound ASOs may be determined before proceeding to the elution step (see below). The methods for detection will depend upon the label or tag incorporated into the ASOs. For example, radioactively labelled or chemiluminescent ASOs that have bound to the target DNA can be detected by exposure of the filter to X-ray film. Alternatively, ASOs containing a fluorescent label can be detected by excitation with a laser or lamp-based system at the specific absorption wavelength of the fluorescent reporter.

In a subsequent step, the bound ASOs are eluted from the matrix-bound target DNA. Elution may be accomplished by any means known in the art that destabilizes DNA:DNA hybrids, i.e. lowering salt, raising temperature, exposure to formamide, alkali, etc. In a preferred embodiment, the bound oligonucleotides are eluted by incubating the target DNA-ASO complexes in water, and heating the reaction above the melting temperature of the DNA:DNA hybrids. This obviates the need for further treatment or purification of the eluted ASOs.

In one embodiment, the eluted ASO is directly subjected to DNA sequencing, using a chemical method standard in the art (e.g. Maxim-Gilbert sequencing, Maxam and Gilbert, 1977, Proc. Natl. Acad. Sci., USA, 74:560). This method is particularly applicable when randomly permitted mixtures of ASOs are used.

In another embodiment, the eluted ASOs are identified by enzymatic DNA sequencing (Sanger et al., 1977, Proc. Natl. Acad. Sci., USA, 74:5463). In this case, oligonucleotides are synthesized that contain DNA sequences complementary to the ASOs and additional pre-determined co-linear sequences that act as sequence "tags" (see Example 4 below). Elution of the ASOs from the target DNA is performed in the presence of a mixture of these complementary, "tagged" oligonucleotides. When incubated under Sanger sequencing conditions (see e.g. Example 5 below), the eluted ASOs hybridize to their complementary sequences and act as primers for the sequencing reaction. Determination of the resulting primed sequence "tag" then identifies the ASO(s) present in the reaction.

In a further embodiment, the eluted ASOs are incubated with complementary oligonucleotides that may contain universal primer sequences and/or a sequencing primer sequence with or without an additional "tag" sequence (see Example 4 below). In both cases, initial hybridization of an ASO to its complementary oligonucleotide allows the ASO to serve as the initial primer in a single extension reaction. In one case, the extension product is then used directly as template in a cycle sequencing reaction. Cycle sequencing of the extension products results in amplification of the sequencing products. In designing the complementary oligonucleotides, the sequencing primer is oriented so that sequencing proceeds through the ASO itself, or, alternatively, through the "tag" sequence.

In the second case, the extension product includes a universal primer sequence and a sequencing primer sequence. This extension product is then added to a linear PCR reaction in the presence of universal primer. The oligonucleotides containing complementary sequences to bound ASOs are therefore selectively amplified. In a second step, these amplified sequences are subjected to Sanger sequencing, using the built-in sequencing primer sequence. In this case, the sequencing primer is placed immediately upstream of a "tag" sequence as above. Thus, determination of the "tag" sequence will identify the colinear ASO sequence.

In practicing the present invention, it is not necessary to determine the entire sequence of the ASO or of the complementary tagged oligonucleotide. It is contemplated that 1, 2, or 3 sequencing reactions (instead of the four needed to obtain a complete sequence) will be effective in producing characteristic patterns (similar to "bar codes") to allow the immediate identification of individual ASOs. This approach is applicable to manual sequencing methods using radioactively labelled ASOs, which produce analog or digitized autoradiograms, as well as to automated sequencing methods using non-radioactive reporter molecules, which produce digitized patterns. In either case, comparisons to an established data base can be performed electronically. Thus, by reducing the number of required sequencing reactions, the methods of the present invention facilitate the economical analysis of multiple samples.

The present invention accommodates the simultaneous screening of a large number of potential ASOs in a single reaction. In practice, the actual number of ASOs that are pooled for simultaneous hybridization is determined according to the diagnostic need. For example, in cystic fibrosis (CF), one particular mutation (Δ508) accounts for more than 70% of CF cases. Thus, a preliminary hybridization with a labelled or tagged Δ508-specific ASO according to the present methods, followed by detection of the bound ASO, will identify and eliminate Δ508 alleles. In a second ("phase two") hybridization, a large number of ASOs encoding other, less frequent, CF alleles is performed, followed by elution and sequencing as described above.

In other clinical situations, however, a single mutation that appears with as high a frequency as the Δ508 mutation in CF does not exist. Therefore, pools of ASOs are determined only by the number of independent hybridizations that would be needed in a phase two analysis on a pool positive sample.

In addition, in current clinical practice, different clinical syndromes, e.g. cystic fibrosis, thalassemia, and Gaucher's disease, are screened independently of each other. The present invention, by contrast, accommodates the simultaneous screening of large numbers of DNAs from different patients with a large number of ASOs that are complementary to mutations in more than one potential disease-causing gene.

In the same manner, when clinical indicators suggest infection by a foreign agent or microorganism, the present invention provides for simultaneous screening for a large number of potential foreign DNAs. Furthermore, particular strains, variants, mutants, and the like of one or more microorganisms can also be distinguished by employing appropriate ASOs in the first screening.

The methods of the present invention also make it possible to define potentially novel mutant alleles carried in the DNA of a patient or an invading microorganism, by the use of randomly permuted ASOs in phase one or phase two screening. In this embodiment, elution of the bound ASOs, followed by sequencing, reveals the precise mutant sequence.

The following examples are intended to further illustrate the present invention without limiting the invention thereof.

EXAMPLE 1

Preparation of Target DNA

A) Preparation of Sample DNA from Blood

Whole blood samples collected in high glucose ACD Vacutainers™ (yellow top) were centrifuged and the buffy coat collected. The white cells were lysed with two washed of a 10:1 (v/v) mixture of 14 mM NH4Cl and 1 mM NaHCO3, their nuclei were resuspended in nuclei-lysis buffer (10 mM Tris, pH 8.0, 0.4M NaCl, 2 mM EDTA, 0.5% SDS, 500 ug/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA.)

B) Preparation of Sample DNA from Buccal Cells

Buccal cells were collected on a sterile cytology brush (Scientific Products) or female dacron swab (Medical Packaging Corp.) by twirling the brush or swab on the inner cheek for 30 seconds. DNA was prepared as follows, immediately or after storage at room temperature or at 4° C. The brush or swab was immersed in 600 µl of 50 mM NaOH contained in a polypropylene microcentrifuge tube and vortexed. The tube, still containing the brush or swab, was heated at 95° C. for 5 min, after which the brush or swab was carefully removed. The solution containing DNA was then neutralized with 60 µl of 1M Tris, pH 8.0, and vortexed again (Mayall et al., J. Med. Genet. 27:658, 1990). The DNA was stored at 4° C.

C) Amplification of Target DNA Prior to Hybridization

DNA from patients with CF was amplified by PCR in a Perkin-Elmer Cetus 9600 Thermocycler. Five primer sets were used to simultaneously amplify relevant regions of exons 4, 10, 20, and 21 of the cystic fibrosis transmembrane conductance regulator (CFTR) gene (Richards et al., Human Mol. Gen. 2:159, 1993). The 50 µl PCR reaction mix contained the following components: 0.2–1 µg CF patient DNA, 10 mM Tris pH 8.3, 50 mM KCl, 1.5 mM MgCl2, 0.01% (w/v) gelatin, 200 µM of each deoxynucleotide triphosphate, 0.4 µM of each amplification primer, and 2.5 units of Taq polymerase. An initial denaturation was performed by incubation at 94° C. for 20 seconds, followed by 28 cycles of amplification, each consisting of 10 seconds at 94° C., 10 seconds at 55° C., 10 seconds at 74° C., and a final soak at 74° C. for 5 min. Following amplification, 8 µl of the PCR products were electrophoresed in a 2% agarose gel to verify the presence of all five products.

D) Binding of DNA to a Solid Matrix

8 µl of the amplified DNA solution prepared as in C) were added to 50 µl of a denaturing solution (0.5 mM NaOH, 2.0M NaCl, 25 mM EDTA) and spotted onto nylon membrane filters (INC Biotrans). The DNA was then fixed to the membranes by baking the filters at 80° C. for 15 minutes under vacuum.

EXAMPLE 2

Hybridization with Allele-Specific Oligonucleotides

The oligonucleotides shown in Table 1 represent known cystic fibrosis (CF) alleles.

TABLE 1

Mutant ASO Sequences

| ASO | Sequence (17-mer) | |
|---|---|---|
| ΔF508M | 5'ACA/CCA/ATG/ATA/TTT/TC 3' | SEQ. ID. NO. 1 |
| G-542XM | 5'ATT/CCA/CCT/TCT/CAA/AG 3' | SEQ. ID. NO. 2 |
| G551DM | 5'CTC/GTTIGAT/CTC/CAC/TC 3' | SEQ. ID. NO. 3 |
| R553XM | 5'CTC/ATTIGAC/CTC/CAC/TC 3' | SEQ. ID. NO. 4 |
| W1282XM | 5'CTT/TCC/TTC/ACT/GTT/GC 3' | SEQ. ID. NO. 5 |
| N1303KM | 5'TCA/TAG/GGA/TCC/AAC/TT 3' | SEQ. ID. NO. 6 |
| Δ1507M | 5'ACA/CCA/AAG/ATA/TTT/TC 3' | SEQ. ID. NO. 7 |
| R117HM | 5'CGA/TAG/AGT/GTT/CCT/CC 3' | SEQ. ID. NO. 8 |
| 621 + 1M | 5'GCA/AGG/AAG/TAT/TAA/CT 3' | SEQ. ID. NO. 9 |
| S549NM | 5'CTC/GTT/GAC/CTC/CAT/TC 3' | SEQ. ID. NO. 10 |
| R560TM | 5'TAT/TCA/CGT/TGC/TAA/AG 3' | SEQ. ID. NO. 11 |
| 1717-1M | 5'GGA/GAT/GTC/TTA/TTA/CC 3' | SEQ. ID. NO. 12 |
| 3849 + 10M | 5'ACT/CAC/CAT/TTT/AAT/AC 3' | SEQ. ID. NO. 13 |
| 3905 + TM | 5'GTA/GTC/TCA/AAA/AAA/GC 3' | SEQ. ID. NO. 14 |
| R347PM | 5'GTG/ACC/GCC/ATG/GGC/AG 3' | SEQ. ID. NO. 15 |
| 1078dTBM | 5'CAC/CAC/AAG/AAC/CCT/GA 3' | SEQ. ID. NO. 16 |
| 2789 + 5GAM | 5'GGA/ATA/TTC/ACT/TTC/CA 3' | SEQ. ID. NO. 17 |
| 3849 + 4CM | 5'GCA/GTG/TTC/AAA/TCC/CA 3' | SEQ. ID. NO. 18 |
| 711 + 1GTM | 5'CAT/AAT/TCA/TCA/AAT/TT 3' | SEQ. ID. NO. 19 |
| R1162XM | 5'CTC/AGC/TCA/CAG/ATC/GC 3' | SEQ. ID. NO. 20 |
| 1898 + 1GAM | 5'CAT/ATC/TTT/CAA/ATA/TT 3' | SEQ. ID. NO. 21 |
| 3659dCM | 5'CTT/GTA/GGT/TTA/CCT/TC 3' | SEQ. ID. NO. 22 |
| G85EM | 5'GAT/TTC/ATA/GAA/CAT/AA 3' | SEQ. ID. NO. 23 |
| 2184dAM | 5'GAT/TGC/TTT/TTG/TTT/CT 3' | SEQ. ID. NO. 24 |
| A455EM | 5'AAC/CTC/CAA/CAA/CTG/TC 3' | SEQ. ID. NO. 25 |
| R334WM | 5'TTC/CAG/AGG/ATG/ATT/CC 3' | SEQ. ID. NO. 26 |
| Y122XBM | 5'AGT/TAA/ATC/GCG/ATA/GA 3' | SEQ. ID. NO. 27 |
| S549RBM | 5'TCC/CCT/CAG/TGT/GAT/TC 3' | SEQ. ID. NO. 28 |
| Q493XM | 5'ACT/AAG/AAC/AGA/ATG/AA 3' | SEQ. ID. NO. 29 |
| V520FM | 5'GAT/GAA/GCT/TCT/GTA/TC 3' | SEQ. ID. NO. 30 |
| Y1092XM | 5'ACA/GTT/ACA/AGA/ACC/AG 3' | SEQ. ID. NO. 31 |
| R347HM | 5'GTG/ACC/GCC/ATG/TGC/AG 3' | SEQ. ID. NO. 32 |
| ΔF508N | 5'CAT/AGG/AAA/CAC/CAA/AG 3' | SEQ. ID. NO. 33 |
| G542XN | 5'ATT/CCA/CCT/TCT/CCA/AG 3' | SEQ. ID. NO. 34 |
| G551DN | 5'CTC/GTT/GAC/CTC/CAC/TC 3' | SEQ. ID. NO. 35 |
| R553XN | See G551 DN sequence | |
| W1282XN | 5'CTT/TCC/TCC/ACT/GTT/GC 3' | SEQ. ID. NO. 36 |
| N1303KN | 5'TCA/TAG/GGA/TCC/AAG/TT 3' | SEQ. ID. NO. 37 |
| Δ507N | 5'ACA/CCA/AAG/ATG/ATA/Tr 3' | SEQ. ID. NO. 38 |
| R117HN | 5'CGA/TAG/AGC/GTT/CCT/CC 3' | SEQ. ID. NO. 39 |
| 621 + 1N | 5'GCA/AGG/AAG/TAT/TAC/CT 3' | SEQ. ID. NO. 40 |
| S549NN | 5'See G551 DN sequence | |
| R560TN | 5'TAT/TCA/CCT/TGC/TAA/AG 3' | SEQ. ID. NO. 41 |
| 1717-1N | 5'GGA/GAT/GTC/CTA/TTA/CC 3' | SEQ. ID. NO. 42 |
| 3849 + 10N | 5'ACT/CGC/CAT/TTT/AAT/AC 3' | SEQ. ID. NO. 43 |
| 3905 + TN | 5'GTA/GTC/TCA/AAA/AAG/CT 3' | SEQ. ID. NO. 44 |
| R347PN | 5'GTG/ACC/GCC/ATG/CGC/AG 3' | SEQ. ID. NO. 45 |
| 1078dTBN | 5'CAC/CAC/AAA/GAA/CCC[rG 3' | SEQ. ID. NO. 46 |
| 2789 + 5GAN | 5'GGA/ATA/CTC/ACT/TTC/CA 3' | SEQ. ID. NO. 47 |
| 3849 + 4CN | 5'GCA/GTG/TTC/AAA/TCT/CA 3' | SEQ. ID. NO. 48 |
| 711 + 1GTN | 5'CAT/ACT/TCA/TCA/AAT/TT 3' | SEQ. ID. NO. 49 |
| R1162XN | 5'CTC/GGC/TCA/CAG/ATC/GC 3' | SEQ. ID. NO. 50 |
| 1898 + 1GAN | 5'CAT/ACC/TTT/CAA/ATA/TT 3' | SEQ. ID. NO. 51 |
| 3659dCN | 5'CTT/GGT/AGG/TTT/ACC/TT 3' | SEQ. ID. NO. 52 |
| G85EN | 5'GAT/TCC/ATA/GAA/CAT/AA 3' | SEQ. ID. NO. 53 |
| 2184dAN | 5'GAT/TGT/TTT/TTT/GTT/TC 3' | SEQ. ID. NO. 54 |
| A455EN | 5'AAC/CGC/CAA/CAA/CTG/TC 3' | SEQ. ID. NO. 55 |
| R334WN | 5'TTC/CGG/AGG/ATG/ATT/CC 3' | SEQ. ID. NO. 56 |
| Y122XBN | 5'AGA/TAA/ATC/GCG/ATA/GA 3' | SEQ. ID. NO. 57 |
| S549RBN | 5'TCC/ACT/CAG/TGT/GAT/TC 3' | SEQ. ID. NO. 58 |
| Q493XN | 5'ACT/GAG/AAC/AGA/ATG/AA 3' | SEQ. ID. NO. 59 |
| V520FN | 5'GAT/GAC/GCT/TCT/GTA/TC 3' | SEQ. ID. NO. 60 |
| Y1092XN | 5'ACA/GGT/ACA/AGA/ACC/AG 3' | SEQ. ID. NO. 61 |
| R347HN | see R347PN sequence | |

A) Hybridizations

The oligonucleotides shown in Table 1 were chemically synthesized using an automated synthesizer, and were radiolabelled with $^{32}P$ with polynucleotide kinase, using methods that are standard in the art.

Hybridizations were carried out in plastic bags containing the filters prepared as in Example 1D above, to which pooled radiolabelled ASOs were added in a TMAC hybridization buffer (3.0M TMAC, 0.6% SDS, 1 mM EDTA, 10 mM sodium phosphate pH 6.8, 5X Denhardt's Solution, and 40 µg/ml yeast RNA). ASO concentrations in the pools ranged from 0.03 to 0.15 pmol/ml hybridization solution.

Hybridizations were allowed to proceed overnight at 52° C., with agitation. The membranes were then removed from the bags and washed for 20 min at room temperature with wash buffer (3.0M TMAC, 0.6% SDS, 1 mM EDTA, 10 mM sodium phosphate pH 6.8), followed by a second wash in the same buffer for 20 min at 52° C. The membranes were then dried and exposed to Kodak X-OMAT film.

B) Results

The specificity of hybridization using the conditions described in A) was evaluated by probing amplified samples from individuals of known genotype with 11 of the ASOs described above (Table 1). The results are shown in FIG. 1. Each ASO hybridized specifically only to samples carrying the complementary mutant sequence (lane 1 in each case) and not to samples not containing that sequence (as in lanes 2–6, containing wild-type "normal" sequences).

When pools of ASOs were used, identical results were observed (FIG. 2). In this experiment, four separate hybridizations were performed, containing ASOs included in Table 1. In this case, the samples spotted in lanes 1–12, rows B and C, were negative for all mutations (bottom three panels), but were positive for the wild-type Δ508 sequence (top panel.)

Figures 3A, 3B:
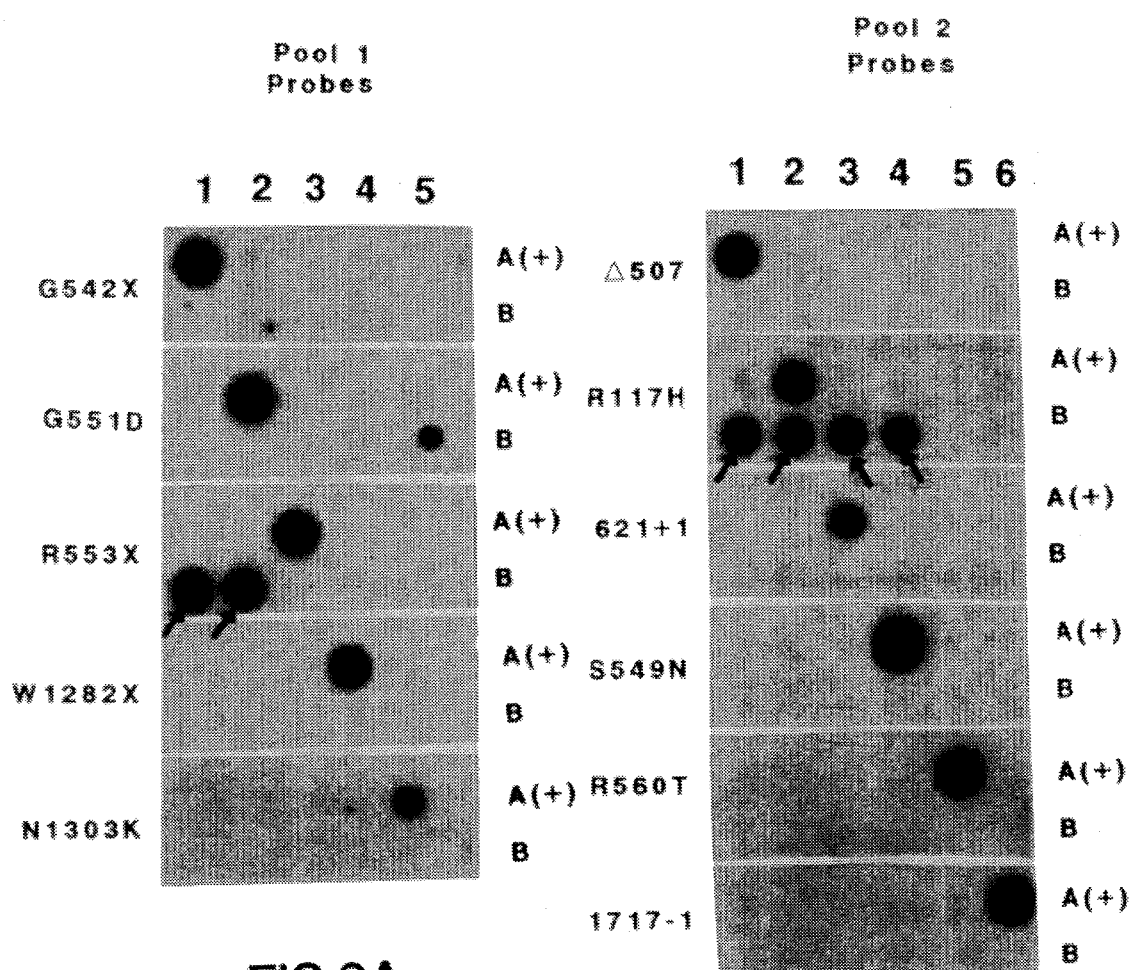
FIG. 3 shows the identification of specific mutations in pool-positive samples identified in FIG. 1. The top row of each filter contains positive control samples for ASOs in pool 1 and pool 2 as indicated. Pool 1, lane 1, G542X; lane 2, G551D; lane 3, R553X; lane 4, W1282X; lane 5, N1303K. Pool 2, lane 1, Δ507; lane 2, R117H; lane 3, 621+1 G→T; lane 4, S549N; lane 5, R560T; lane 6, 1717-1 G→A. Row B contains pool-1 or pool-2 positive patient samples. Pool 1, lanes 1 and 2 contain sample 4, lanes D and E from FIG. 1. Pool 2, lanes 1 and 2 contains sample 3, lanes D and E from FIG. 2. Lanes 3 and 4 contain sample 5, lanes D and E from FIG. 2.

By contrast, the sample spotted in lane 6, rows D and E, was positive for the Δ508 mutation and negative for the wild-type sequence, indicating that this patient was homozygous for the Δ508 allele. Similarly, the sample in lane 4, rows D and E, was pool-1 positive, while the samples in lanes 3 and 5, rows D and E, were pool-2 positive. Subsequent individual hybridizations of the latter samples with each probe in pool 1 and pool 2 verified that the pool-positive hybridizations were in fact due to hybridization with a single member of the pool (FIG. 3.) That is, the sample from lane 4, rows D and E of FIG. 2 was shown to hybridize specifically with the R553X ASO, while the samples in lanes 3 and 5, D and E of FIG. 2 hybridized specifically with the R117H ASO.

EXAMPLE 3

Elution of Bound ASOs

The present invention encompasses a method for hybridizing a large number of potential ASOs to a patient's DNA in a single hybridization reaction. In a subsequent step, the ASOs that have bound to the target DNA are eluted and sequenced, with or without prior amplification.

Pool-positive samples from hybridizations performed as in Example 2 are treated as follows: Positive spots are excised in the form of discs from the nylon membrane using a standard single hole paper punch. Each of the excised membrane discs is then placed in separate 1.5 ml microcentrifuge tubes containing 100 µl of sterile water, and the tubes are incubated at 100° C. for 15 minutes (FIG. 4.)

EXAMPLE 4

Design of Complementary Oligonucleotides for Identification of Bound ASOs

In practicing the present invention, the sequence of eluted ASOs may be determined directly using chemical sequencing. Alternatively, eluted ASOs may be used in conjunction with complementary oligonucleotides that contain other sequences in addition to sequences complementary to the ASOs. In these cases, the eluted ASOs serve as primers to form extension products that contain the additional sequences, and the extension products are subjected to DNA sequencing.

Following are several embodiments of complementary oligonucleotides that contain the complement of the R334W CF mutation-specific ASO (Table 1).

Version 1: Eluted ASO as sequencing primer

3'-AAGGTCTCCTACTAAGG- TCTCGCTTCGTTTCATCTCATCTCG-5'     SEQ.ID.NO.62
    ASO complement             "Tag"

In this embodiment, the eluted ASO is incubated with the complementary oligonucleotide in a Sanger sequencing reaction, and the sequence is determined directly.

Version 2: Cycle sequencing of eluted ASO

3'-AAGGTCTCCTACTAAGG- TCTCGCTTCGTTTCATCTCATCTCG-
    ASO complement             "Tag"

ATCGATCGATCGATCGATCGATCG-5'     SEQ.ID.NO.63
Universal Primer Sequence

In this embodiment, the eluted ASO serves as a primer for a single extension reaction. The extension product is then subjected to cycle sequencing, using the universal primer to prime the sequencing reaction (see Example 5 below.)

Version 3: Amplification of complementary oligonucleotide for Sanger sequencing

3'-AAGGTCTCCTACTAAGG-CGCCAGGGTTTTCCCAGTCA-
    ASO complement        "sequencing target"

TCTCGCTTCGTTCATCTCATCTCG-ATCGATCGATCGATCGATCGA-5'    SEQ.ID.NO.64
    "Tag"        Universal Primer Sequence In this embodiment, the eluted ASO serves as a primer for a single extension reaction. The extension product is then amplified using the universal primer sequence and the eluted ASO as amplification primers. Finally, the amplification products are subjected to Sanger sequencing using as a primer an oligonucleotide corresponding to the sequencing target (see Example 6 below.)

EXAMPLE 5

Cycle Sequencing of Eluted ASOs

A) Extension Reaction

An eluted mutation-specific oligonucleotide, designated R334W and having the sequence 5'-TTCCAGAGGATGAT-TCC-3' SEQ.ID.NO.65 is added to a reaction mix containing reaction components necessary for a single round of extension. The complementary oligonucleotide (Version 2 in Example 4 above) contains a universal primer sequence at its 5' end, separated by 25–30 bases from the complement to R334W at its 3' end. The extension reaction contains the following components:

25 μl eluted ASO

5 μl 10X buffer (0.5 mM Tris-HCl pH 7.5, 0.1M MgCl$_2$, 10 mM dithiothreitol)

1 μl dNTPs (2.5 mM each)

1 μl complementary oligonucleotides (100 ng/ml)

13 μl H$_2$O

1 μl Klenow fragment of DNA polymerase (10 U/μl)

The reaction is allowed to proceed at room temperature for 30 minutes.

B) Cycle Sequencing

An aliquot of the above reaction is added to a PCR reaction mix containing two or more dideoyxnucleotide analogues (ddNTPs), according to the following protocol:

10 μl extension products

5 μl 10X buffer (300 mM Tris-HCl pH 9.0, 50 mM MgCl$_2$, 300 mM KCl)

5 μl universal primer (1 pmole)

10 μl 2 mM ddATP, ddCTP, ddGTP; 100 μM dATP, dCTP, dGTP, dTTP

19 μl H$_2$O

1 μl Taq polymerase (10 U/μl)

30 cycles of amplification are performed, creating a heterogeneous population of random termination products that terminate at positions corresponding to nucleotides downstream of the universal primer sequence. The products of the PCR reaction are then separated in a denaturing polyacrylamide gel, creating a banding pattern specific for this ASO. The electrophoretic pattern is analyzed by autoradiography or fluorimetry.

EXAMPLE 6

Amplification and Sequencing of Complementary Oligonucleotides

An eluted mutation-specific oligonucleotide, designated R334W and having the sequence 5'-TTCCAGAGGATGAT-TCC-3' is added to a reaction mix containing reaction components for extension as in Example 5, Step A. The complementary oligonucleotide (Version 3 in Example 4 above) contains a universal primer sequence at its 5' end, a "tag" sequence, "sequencing target" sequence, followed by the complement to R334W at its 3' end. Following the extension reaction, an aliquot of the reaction is added to an amplification mixture containing the following components:

3 μl extension products

1 μl universal amplification primer (10 μM)

2.5 μl dATP, dTTP, dCTP, dGTP (2 mM each)

2 μl 40 mM MgCl$_2$

5 μl 100 mM Tris-HCl pH 8.3, 500 mM KCl 26.4 μl H$_2$O 0.1 μl Amphitaq DNA polymerase (5 U/ml).

The reaction is then subjected to 35 cycles of amplification, using a GeneAmp PCR System 9600 Thermocycler. 2 μl of the amplification products are then removed and subjected to Sanger sequencing, using the Sanger sequencing primer.

I claim:

1. A method for high-throughput screening of mammalian genomic DNA samples to identify one or more genetic alterations in one or more target DNA sequences present in said samples, comprising the steps of:
   (i) immobilizing a plurality of said mammalian genomic DNA samples on a solid-phase support;
   (ii) simultaneously hybridizing said immobilized DNA samples with a multiplicity of synthetic oligonucleotides of equivalent length, each of said oligonucleotides comprising a variant sequence of one of said target DNA sequences;
   (iii) removing oligonucleotides that do not hybridize to said immobilized DNA samples;
   (iv) individually eluting from each of said immobilized DNA samples oligonucleotides that hybridize to said samples; and
   (v) determining the sequence of said individually eluted oligonucleotides;
   wherein the sequence identifies said one or more genetic alterations.

2. The method of claim 1, wherein said alterations comprise nucleotide insertions, deletions, or substitutions.

3. The method of claim 1, wherein said mammalian DNA samples are derived from humans suffering from a genetic disease.

4. The method of claim 3, wherein said disease is selected from the group consisting of cystic fibrosis, beta-thalassemia, Tay-Sachs disease, sickle cell anemia, and Gaucher's disease.

5. The method of claim 1, wherein said oligonucleotides are from about 16 to about 25 nucleotides in length.

6. The method of claim 1, wherein at least one of said target DNA sequences is amplified from said genomic DNA samples prior to said immobilizing step to form an amplified sequence.

7. The method of claim 6, wherein said amplified sequence is from about 80 bp to about 30 kbp in length.

8. The method of claim 1, wherein said solid-phase support is selected from the group consisting of nitrocellulose filter, nylon filter, glass beads, and plastic.

9. The method of claim 1, wherein said hybridizing step is performed in the presence of an effective concentration of an agent that eliminates disparities in the melting temperatures of hybrids between said oligonucleotides and said target DNA.

10. The method of claim 9, wherein said agent is a quaternary ammonium salt.

11. The method of claim 10, wherein said quaternary ammonium salt is tetramethyl ammonium chloride.

12. The method of claim 1, wherein said determining step comprises chemical sequencing.

13. The method of claim 1, wherein said determining step comprises
   (a) contacting said eluted oligonucleotides with a multiplicity of complementary oligonucleotides comprising (i) sequences complementary to said eluted oligonucleotides and (ii) additional predetermined colinear sequences;
   (b) performing enzymatic sequencing, wherein said eluted oligonucleotides serve as primers and said complementary oligonucleotides serve as templates for said enzymatic sequencing; and
   (c) identifying said predetermined colinear sequences as an indicator of the presence of said eluted oligonucleotides.

14. The method of claim 1, wherein said determining step comprises
   (a) contacting said eluted oligonucleotides with a multiplicity of complementary oligonucleotides comprising (i) sequences complementary to said eluted oligonucleotides and (ii) additional predetermined colinear sequences;
   (b) performing a single extension reaction, wherein said eluted oligonucleotides serve as primers and said complementary oligonucleotides serve as templates for said extension reaction;
   (c) performing enzymatic sequencing of the products of said extension reaction; and
   (d) identifying said predetermined colinear sequences as an indicator of the presence of said eluted oligonucleotides.

15. The method of claim 14, further comprising amplifying said extension products prior to said sequencing step.

16. A method for high-throughput screening of DNA samples from patients to identify one or more target DNA sequences present in said samples, comprising the steps of:
   (i) immobilizing a plurality of said DNA samples on a solid-phase support;
   (ii) hybridizing said immobilized DNA samples simultaneously with a multiplicity of synthetic oligonucleotides of equivalent length, each of said oligonucleotides comprising a variant sequence of one of said target DNA sequences;
   (iii) removing oligonucleotides that do not hybridize to said immobilized DNA samples;
   (iv) individually eluting from each of said immobilized DNA samples oligonucleotides that hybridize to said samples; and
   (v) determining the sequence of said individually eluted oligonucleotides;
   wherein the sequence identifies said one or more genetic alterations.

17. The method of claim 16, wherein said target DNA is selected from the group consisting of viral, bacterial, fungal, and protozoal DNA.

18. A method for high-throughput screening of mammalian genomic DNA samples to identify novel genetic alterations in one or more target DNA sequences present in said samples, comprising the steps of:
   (i) immobilizing a plurality of said mammalian genomic DNA samples on a solid-phase support;
   (ii) hybridizing said immobilized DNA samples simultaneously with a multiplicity of synthetic oligonucleotides of equivalent length, said oligonucleotides comprising randomly permuted variants of at least one of said target DNA sequences;
   (iii) removing oligonucleotides that do not hybridize to said immobilized DNA samples;
   (iv) individually eluting from each of said immobilized DNA samples oligonucleotides that hybridize to said samples; and
   (v) determining the sequence of said individually eluted oligonucleotides;
   wherein the sequence identifies said one or more genetic alterations.

* * * * *

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to mRNA (vi) ORIGINAL SOURCE:
    (A) ORGANISM: Homo sapien (vii) IMMEDIATE SOURCE:
    (B) CLONE: DELTA F508M (xi) SEQUENCE DESCRIPTION: SEQ ID NO:1:

ACACCAATGA TATTTTC    17

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapien (vii) IMMEDIATE SOURCE:
        (B) CLONE: G542XM (xi) SEQUENCE DESCRIPTION: SEQ ID NO:2:

ATTCCACCTT CTCAAAG    17

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapien (vii) IMMEDIATE SOURCE:
        (B) CLONE: G551DM (xi) SEQUENCE DESCRIPTION: SEQ ID NO:3:

CTCGTTGATC TCCACTC    17

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapien (vii) IMMEDIATE SOURCE:
        (B) CLONE: R553XM (xi) SEQUENCE DESCRIPTION: SEQ ID NO:4:

CTCATTGACC TCCACTC    17

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single ( D ) TOPOLOGY: linear ( i i ) MOLECULE TYPE: cDNA ( v i ) ORIGINAL SOURCE:
    ( A ) ORGANISM: Homo sapien ( v i i ) IMMEDIATE SOURCE:
    ( B ) CLONE: W1282XM ( x i ) SEQUENCE DESCRIPTION: SEQ ID NO:5:

CTTTCCTTCA CTGTTGC     17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: N1303KM ( x i ) SEQUENCE DESCRIPTION: SEQ ID NO:6:

TCATAGGGAT CCAACTT     17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: DELTA 1507M ( x i ) SEQUENCE DESCRIPTION: SEQ ID NO:7:

ACACCAAAGA TATTTTC     17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: R117HM ( x i ) SEQUENCE DESCRIPTION: SEQ ID NO:8:

CGATAGAGTG TTCCTCC     17

( 2 ) INFORMATION FOR SEQ ID NO:9:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapien ( v i i ) IMMEDIATE SOURCE:
    ( B ) CLONE: 621+1M ( x i ) SEQUENCE DESCRIPTION: SEQ ID NO:9:

GCAAGGAAGT ATTAACT                         17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: S549NM ( x i ) SEQUENCE DESCRIPTION: SEQ ID NO:10:

CTCGTTGACC TCCATTC                         17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: R560TM ( x i ) SEQUENCE DESCRIPTION: SEQ ID NO:11:

TATTCACGTT GCTAAAG                         17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: 1717-1M ( x i ) SEQUENCE DESCRIPTION: SEQ ID NO:12:

GGAGATGTC TTATTACC                         17

( 2 ) INFORMATION FOR SEQ ID NO:13:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapien ( v i i ) IMMEDIATE SOURCE:
    ( B ) CLONE: 3849+10M ( x i ) SEQUENCE DESCRIPTION: SEQ ID NO:13:

ACTCACCATT TTAATAC    17

( 2 ) INFORMATION FOR SEQ ID NO:14:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapien ( v i i ) IMMEDIATE SOURCE:
    ( B ) CLONE: 3905+TM ( x i ) SEQUENCE DESCRIPTION: SEQ ID NO:14:

GTAGTCTCAA AAAAAGC    17

( 2 ) INFORMATION FOR SEQ ID NO:15:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapien ( v i i ) IMMEDIATE SOURCE:
    ( B ) CLONE: R347PM ( x i ) SEQUENCE DESCRIPTION: SEQ ID NO:15:

GTGACCGCCA TGGGCAG    17

( 2 ) INFORMATION FOR SEQ ID NO:16:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapien ( v i i ) IMMEDIATE SOURCE:
    ( B ) CLONE: 1078dTBM ( x i ) SEQUENCE DESCRIPTION: SEQ ID NO:16:

CACCACAAGA ACCCTGA                                                                                      17

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: 2789+5GAM ( x i ) SEQUENCE DESCRIPTION: SEQ ID NO:17:

GGAATATTCA CTTTCCA                                                                                      17

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: 3849+4CM ( x i ) SEQUENCE DESCRIPTION: SEQ ID NO:18:

GCAGTGTTCA AATCCCA                                                                                      17

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: 711+1GTM ( x i ) SEQUENCE DESCRIPTION: SEQ ID NO:19:

CATAATTCAT CAAATTT                                                                                      17

( 2 ) INFORMATION FOR SEQ ID NO:20:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:

(A) ORGANISM: Homo sapien (vii) IMMEDIATE SOURCE:
(B) CLONE: R1162XM (xi) SEQUENCE DESCRIPTION: SEQ ID NO:20:

CTCAGCTCAC AGATCGC                                                          17

(2) INFORMATION FOR SEQ ID NO:21:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapien (vii) IMMEDIATE SOURCE:
(B) CLONE: 1898+1GAM (xi) SEQUENCE DESCRIPTION: SEQ ID NO:21:

CATATCTTTC AAATATT                                                          17

(2) INFORMATION FOR SEQ ID NO:22:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapien (vii) IMMEDIATE SOURCE:
(B) CLONE: 3659dCM (xi) SEQUENCE DESCRIPTION: SEQ ID NO:22:

CTTGTAGGTT TACCTTC                                                          17

(2) INFORMATION FOR SEQ ID NO:23:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapien (vii) IMMEDIATE SOURCE:
(B) CLONE: G85EM (xi) SEQUENCE DESCRIPTION: SEQ ID NO:23:

GATTTCATAG AACATAA                                                          17

(2) INFORMATION FOR SEQ ID NO:24:

(i) SEQUENCE CHARACTERISTICS:
(A) LENGTH: 17 base pairs
(B) TYPE: nucleic acid
(C) STRANDEDNESS: single
(D) TOPOLOGY: linear ( i i ) MOLECULE TYPE: cDNA ( v i ) ORIGINAL SOURCE:
    ( A ) ORGANISM: Homo sapien ( v i i ) IMMEDIATE SOURCE:
    ( B ) CLONE: 2184dAM ( x i ) SEQUENCE DESCRIPTION: SEQ ID NO:24:

GATTGCTTTT TGTTTCT                                                            17

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: A455EM ( x i ) SEQUENCE DESCRIPTION: SEQ ID NO:25:

AACCTCCAAC AACTGTC                                                         17

( 2 ) INFORMATION FOR SEQ ID NO:26:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: R334WM ( x i ) SEQUENCE DESCRIPTION: SEQ ID NO:26:

TTCCAGAGG ATGATTCC                                                       17

( 2 ) INFORMATION FOR SEQ ID NO:27:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: Y122XBM ( x i ) SEQUENCE DESCRIPTION: SEQ ID NO:27:

AGTTAAATCG CGATAGA                                                       17

( 2 ) INFORMATION FOR SEQ ID NO:28:

( i ) SEQUENCE CHARACTERISTICS:

( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapien ( v i i ) IMMEDIATE SOURCE:
            ( B ) CLONE: S549RBM ( x i ) SEQUENCE DESCRIPTION: SEQ ID NO:28:

TCCCCTCAGT GTGATTC                                                      17

( 2 ) INFORMATION FOR SEQ ID NO:29:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapien ( v i i ) IMMEDIATE SOURCE:
            ( B ) CLONE: Q493XM ( x i ) SEQUENCE DESCRIPTION: SEQ ID NO:29:

ACTAAGAACA GAATGAA                                                      17

( 2 ) INFORMATION FOR SEQ ID NO:30:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapien ( v i i ) IMMEDIATE SOURCE:
            ( B ) CLONE: V520FM ( x i ) SEQUENCE DESCRIPTION: SEQ ID NO:30:

GATGAAGCTT CTGTATC                                                      17

( 2 ) INFORMATION FOR SEQ ID NO:31:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapien ( v i i ) IMMEDIATE SOURCE:
            ( B ) CLONE: Y1092XM ( x i ) SEQUENCE DESCRIPTION: SEQ ID NO:31:

ACAGTTACAA GAACCAG                                                      17

( 2 ) INFORMATION FOR SEQ ID NO:32:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: R347HM ( x i ) SEQUENCE DESCRIPTION: SEQ ID NO:32:

GTGACCGCCA TGTGCAG                         17

( 2 ) INFORMATION FOR SEQ ID NO:33:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: DELTA F508N ( x i ) SEQUENCE DESCRIPTION: SEQ ID NO:33:

CATAGGAAAC ACCAAAG                         17

( 2 ) INFORMATION FOR SEQ ID NO:34:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: G542XN ( x i ) SEQUENCE DESCRIPTION: SEQ ID NO:34:

ATTCCACCTT CTCCAAG                         17

( 2 ) INFORMATION FOR SEQ ID NO:35:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: G551DN ( x i ) SEQUENCE DESCRIPTION: SEQ ID NO:35:

CTCGTTGACC TCCACTC 17

( 2 ) INFORMATION FOR SEQ ID NO:36:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: W1282XN ( x i ) SEQUENCE DESCRIPTION: SEQ ID NO:36:

CTTTCCTCCA CTGTTGC 17

( 2 ) INFORMATION FOR SEQ ID NO:37:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: N1303KN ( x i ) SEQUENCE DESCRIPTION: SEQ ID NO:37:

TCATAGGGAT CCAAGTT 17

( 2 ) INFORMATION FOR SEQ ID NO:38:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: DELTA 1507N ( x i ) SEQUENCE DESCRIPTION: SEQ ID NO:38:

ACACCAAAGA TGATATT 17

( 2 ) INFORMATION FOR SEQ ID NO:39:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien (v i i) IMMEDIATE SOURCE:
    (B) CLONE: R117HN (x i) SEQUENCE DESCRIPTION: SEQ ID NO:39:

CGATAGAGCG TTCCTCC                                                                17

(2) INFORMATION FOR SEQ ID NO:40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: 621+1N (x i) SEQUENCE DESCRIPTION: SEQ ID NO:40:

GCAAGGAAGT ATTACCT                                                                17

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: R560TN (x i) SEQUENCE DESCRIPTION: SEQ ID NO:41:

TATTCACCTT GCTAAAG                                                                17

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: 1717-1N (x i) SEQUENCE DESCRIPTION: SEQ ID NO:42:

GGAGATGTCC TATTACC                                                                17

(2) INFORMATION FOR SEQ ID NO:43:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
　　(A) ORGANISM: Homo sapien (v i i) IMMEDIATE SOURCE:
　　(B) CLONE: 3849+10N (x i) SEQUENCE DESCRIPTION: SEQ ID NO:43:

ACTCGCCATT TTAATAC				17

(2) INFORMATION FOR SEQ ID NO:44:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (i i) MOLECULE TYPE: cDNA (v i) ORIGINAL SOURCE:
　　　　(A) ORGANISM: Homo sapien (v i i) IMMEDIATE SOURCE:
　　　　(B) CLONE: 3905+TN (x i) SEQUENCE DESCRIPTION: SEQ ID NO:44:

GTAGTCTCAA AAAAGCT				17

(2) INFORMATION FOR SEQ ID NO:45:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (i i) MOLECULE TYPE: cDNA (v i) ORIGINAL SOURCE:
　　　　(A) ORGANISM: Homo sapien (v i i) IMMEDIATE SOURCE:
　　　　(B) CLONE: R347PN (x i) SEQUENCE DESCRIPTION: SEQ ID NO:45:

GTGACCGCCA TGCGCAG				17

(2) INFORMATION FOR SEQ ID NO:46:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (i i) MOLECULE TYPE: cDNA (v i) ORIGINAL SOURCE:
　　　　(A) ORGANISM: Homo sapien (v i i) IMMEDIATE SOURCE:
　　　　(B) CLONE: 1078dTBN (x i) SEQUENCE DESCRIPTION: SEQ ID NO:46:

CACCACAAAG AACCCTG				17

(2) INFORMATION FOR SEQ ID NO:47:

(i) SEQUENCE CHARACTERISTICS:
　　　　(A) LENGTH: 17 base pairs ( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapien ( v i i ) IMMEDIATE SOURCE:
( B ) CLONE: 2789+5GAN ( x i ) SEQUENCE DESCRIPTION: SEQ ID NO:47:

GGAATACTCA CTTTCCA    17

( 2 ) INFORMATION FOR SEQ ID NO:48:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapien ( v i i ) IMMEDIATE SOURCE:
( B ) CLONE: 3849+4CN ( x i ) SEQUENCE DESCRIPTION: SEQ ID NO:48:

GCAGTGTTCA AATCTCA    17

( 2 ) INFORMATION FOR SEQ ID NO:49:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapien ( v i i ) IMMEDIATE SOURCE:
( B ) CLONE: 711+1GTN ( x i ) SEQUENCE DESCRIPTION: SEQ ID NO:49:

CATACTTCAT CAAATTT    17

( 2 ) INFORMATION FOR SEQ ID NO:50:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapien ( v i i ) IMMEDIATE SOURCE:
( B ) CLONE: R1162XN ( x i ) SEQUENCE DESCRIPTION: SEQ ID NO:50:

CTCGGCTCAC AGATCGC    17

( 2 ) INFORMATION FOR SEQ ID NO:51:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: 1898+1GAN ( x i ) SEQUENCE DESCRIPTION: SEQ ID NO:51:

CATACCTTTC AAATATT 17

( 2 ) INFORMATION FOR SEQ ID NO:52:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: 3659dCN ( x i ) SEQUENCE DESCRIPTION: SEQ ID NO:52:

CTTGGTAGGT TTACCTT 17

( 2 ) INFORMATION FOR SEQ ID NO:53:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: G85EN ( x i ) SEQUENCE DESCRIPTION: SEQ ID NO:53:

GATTCCATAG AACATAA 17

( 2 ) INFORMATION FOR SEQ ID NO:54:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapien ( v i i ) IMMEDIATE SOURCE:
        ( B ) CLONE: 2184dAN ( x i ) SEQUENCE DESCRIPTION: SEQ ID NO:54:

GATTGTTTTT TTGTTTC                                                                                            17

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapien (vii) IMMEDIATE SOURCE:
        (B) CLONE: A455EN (xi) SEQUENCE DESCRIPTION: SEQ ID NO:55:

AACCGCCAAC AACTGTC                                                                                            17

(2) INFORMATION FOR SEQ ID NO:56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapien (vii) IMMEDIATE SOURCE:
        (B) CLONE: R334WN (xi) SEQUENCE DESCRIPTION: SEQ ID NO:56:

TTCCGGAGGA TGATTCC                                                                                            17

(2) INFORMATION FOR SEQ ID NO:57:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapien (vii) IMMEDIATE SOURCE:
        (B) CLONE: Y122XBN (xi) SEQUENCE DESCRIPTION: SEQ ID NO:57:

AGATAAATCG CGATAGA                                                                                            17

(2) INFORMATION FOR SEQ ID NO:58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapien (v i i) IMMEDIATE SOURCE:
    (B) CLONE: S549RBN (x i) SEQUENCE DESCRIPTION: SEQ ID NO:58:

TCCACTCAGT GTGATTC                                                    17

(2) INFORMATION FOR SEQ ID NO:59:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: Q493XN (x i) SEQUENCE DESCRIPTION: SEQ ID NO:59:

ACTGAGAACA GAATGAA                                                    17

(2) INFORMATION FOR SEQ ID NO:60:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: V520FN (x i) SEQUENCE DESCRIPTION: SEQ ID NO:60:

GATGACGCTT CTGTATC                                                    17

(2) INFORMATION FOR SEQ ID NO:61:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: Y1092XN (x i) SEQUENCE DESCRIPTION: SEQ ID NO:61:

ACAGGTACAA GAACCAG                                                    17

(2) INFORMATION FOR SEQ ID NO:62:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
    (A) ORGANISM: Homo sapien (v i i) IMMEDIATE SOURCE:
    (B) CLONE: VERSION 1 ASO TAG (x i) SEQUENCE DESCRIPTION: SEQ ID NO:62:

GCTCTACTCT ACTTTGCTTC GCTCTGGAAT CATCCTCTGG AA                42

(2) INFORMATION FOR SEQ ID NO:63:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: VERSION 2 ASO TAG (x i) SEQUENCE DESCRIPTION: SEQ ID NO:63:

GCTAGCTAGC TAGCTAGCTA GCTAGCTCTA CTCTACTTTG CTTCGCTCTG GAATCATCCT    60

CTGGAA                                                              66

(2) INFORMATION FOR SEQ ID NO:64:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: VERSION 3 ASO TAG (x i) SEQUENCE DESCRIPTION: SEQ ID NO:64:

AGCTAGCTAG CTAGCTAGCT AGCTAGCTCT ACTCTACTTG CTTCGCTCTA CTGACCCTTT    60

TGGGACCGCG GAATCATCCT CTGGAA                                        86

(2) INFORMATION FOR SEQ ID NO:65:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapien (v i i) IMMEDIATE SOURCE:
        (B) CLONE: R334W (x i) SEQUENCE DESCRIPTION: SEQ ID NO:65:

TTCCAGAGGA TGATTCC                                                  17